(12) United States Patent
Hellstern et al.

(10) Patent No.: US 7,615,609 B2
(45) Date of Patent: Nov. 10, 2009

(54) PREPARATION OF SOMATOSTATIN PEPTIDES

(75) Inventors: Heribert Hellstern, Heitersheim (DE); Werner Pachinger, Basel (CH); Walter Prikoszovich, Schoenenbuch (CH); Bernhard Wietfeld, Efringen-Kirchen (DE)

(73) Assignee: Novartis AG, Basel (CH)

( * ) Notice: Subject to any disclaimer, the term of this patent is extended or adjusted under 35 U.S.C. 154(b) by 136 days.

(21) Appl. No.: 10/567,299

(22) PCT Filed: Aug. 6, 2004

(86) PCT No.: PCT/EP2004/008850

§ 371 (c)(1),
(2), (4) Date: Feb. 6, 2006

(87) PCT Pub. No.: WO2005/014624

PCT Pub. Date: Feb. 17, 2005

(65) Prior Publication Data

US 2006/0258838 A1 Nov. 16, 2006

(30) Foreign Application Priority Data

Aug. 8, 2003 (GB) .................................. 0318682.2

(51) Int. Cl.
*C07K 7/64* (2006.01)
(52) U.S. Cl. ....................... 530/317; 530/333
(58) Field of Classification Search ................. 530/317, 530/333
See application file for complete search history.

(56) References Cited

U.S. PATENT DOCUMENTS 4,621,073 A  11/1986  Friedrich et al.
6,214,316 B1  4/2001  Dean
2005/0014686 A1*  1/2005  Albert et al. ................... 514/10

FOREIGN PATENT DOCUMENTS

| EP | 0 255 224 | 2/1988 |
| WO | WO 97/28172 | 8/1997 |
| WO | WO 98/04583 | 2/1998 |
| WO | WO 99/65508 | 12/1999 |
| WO | WO 02/10192 | 2/2002 |

OTHER PUBLICATIONS

Bruns (Eur J. Endocrinol 146, 707, 2002).*
K. D. Kopple, J. Pharm. Sci. 61, 1345-1356 (1972).*
Lambert, John N., Journal of the Chemical Society, Perkin Transactions 1, (5), 471-484, 2001.*
Blackburn, Christopher (Methods in Enzymology 289, 175-198, 1997).*
Mizhiritskii, Michael, Chimica Oggi 20(7/8), 43-45, 2002.*
Beusen et al, "Conformational Mimicry: Synthesis and Solution Conformation of a Cyclic Somatostatin Hexapeptide Containing a Tetrazole cis Amide Bond Surrogate", *Biopolymers*, vol. 36, pp. 181-200 (1995).
Hirschmann et al., "Synthesis of Potent Cyclic Hexapeptide NK-1 Antagonists. Use of a Minilibrary in Transforming a Peptidal Somatostatin Receptor Ligand into an NK-1 Receptor Ligand via a Polyvalent Peptidomimetic", *J Med Chem*, vol. 39, pp. 2441-2448 (1996).
Huang et al., "Main Chain and Side Chain Chiral Methylated Somatostatin Analogs: Syntheses and Conformational Analyses", *J Am Chem Soc*, vol. 114, pp. 9390-9401 (1992).

* cited by examiner

*Primary Examiner*—David Lukton
(74) *Attorney, Agent, or Firm*—Gregory C. Houghton

(57) ABSTRACT

Provided is a process for preparing cyclic somatostatin analogues and the linear intermediates used in this process.

3 Claims, No Drawings

PREPARATION OF SOMATOSTATIN PEPTIDES

The present invention relates to a process for preparing cyclic somatostatin analogues and the intermediates used in this process.

More particularly the invention provides a process for preparing a cyclic somatostatin analogue of formula I

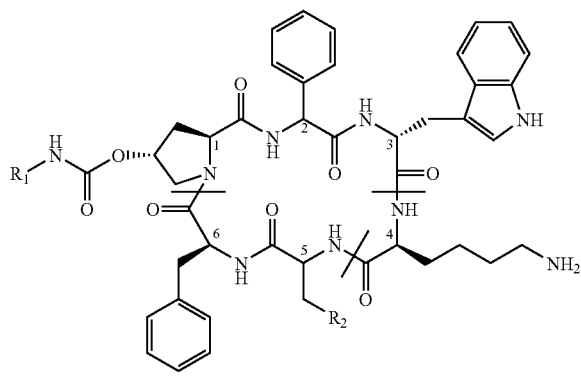

wherein
$R_1$ is —$C_{2-6}$alkylene-$NR_3R_4$, —$C_{2-6}$alkylene-guanidine or —$C_{2-6}$alkylene-COOH wherein each of $R_3$ and $R_4$ independently is H, $C_{1-4}$alkyl, $\Omega$-hydroxy-$C_{2-4}$alkylene or acyl or $R_3$ and $R_4$ form together with the nitrogen atom to which they are attached a heterocyclic group which may comprise a further heteroatom, and
$R_2$ is $Z_1$-$CH_2$—$R_5$, —$CH_2$—CO—O—$CH_2$—$R_5$

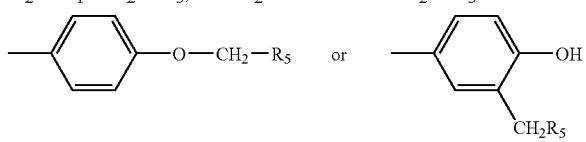

wherein $Z_1$ is O or S and $R_5$ is optionally substituted phenyl,
or a salt thereof.

Any acyl may be e.g. $R_aCO$— wherein $R_a$ is H, $C_{1-4}$alkyl, $C_{2-4}$alkenyl, $C_{3-6}$cycloalkyl or benzyl. When $NR_3R_4$ forms a heterocyclic group, such group may be aromatic or saturated and may comprise one nitrogen or one nitrogen and a second heteroatom selected from nitrogen and oxygen. Preferably the heterocyclic group is e.g. pyridyl or morpholino. $C_{2-6}$alkylene is preferably —$CH_2$—$CH_2$—. When $R_5$ is substituted phenyl, the phenyl ring may be substituted by halogen, methyl, ethyl, methoxy or ethoxy, e.g. in ortho and/or para. Preferably $R_5$ is unsubstituted phenyl.

Amino acids in position 2 and/or 5 may have the D or L configuration. Preferably each of them has the L configuration.

The compounds of formula I may exist e.g. in free or salt form. Salts include acid addition salts with e.g. organic acids, polymeric acids or inorganic acids, for example with hydrochloric acid, acetic acid, lactic acid, aspartic acid, benzoic acid, succinic acid or pamoic acid, or e.g. alkali metal salts when $R_1$ comprises a COOH group. Acid addition salts may exist as mon- or divalent salts, e.g. depending whether 1 or 2 acid equivalents are added to the Compound of formula I in free base form. Preferred salts are the aspartate di-salt or the pamoate monosalt.

The process of production according to the invention comprises a cyclisation step of a corresponding linear peptide in protected form. It has now surprisingly been found that the cyclisation step is particularly dependent on the selection of the 2 terminal amino acids of the corresponding linear peptide. Out of 6 cyclisation possibilities, it has surprisingly been found that the cyclisation between amino acids 3 and 4, or 4 and 5, or 6 and 1 provides significantly interesting results. The cyclisation between amino acids 4 and 5 is particularly preferred. The cyclisation according to the invention between the amino acids 3 and 4, or 4 and 5, or 6 and 1 lead to improved yields with reduced isomerisation at the chiral sites. Furthermore, these cyclisation steps can be performed with less stringent conditions and reactants: e.g. cyclisation through the use of an azide can be avoided.

In a first embodiment of the invention, there is provided a process for preparing a compound of formula I or a salt thereof as indicated above, comprising cyclizing a linear somatostatin analogue of formula II

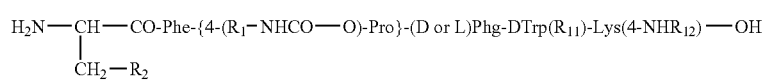

or of formula III

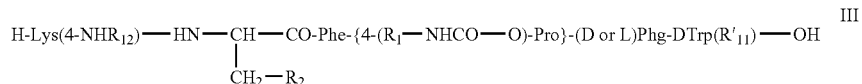

or of formula IV

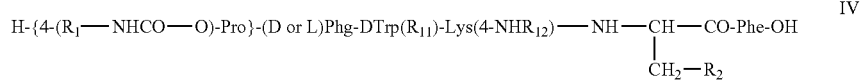

wherein $R_1$ and $R_2$ are as defined, each of $R_{11}$ and $R_{12}$, independently, is an amino protecting group whereby when $R_1$ comprises a terminal $NH_2$, this terminal $NH_2$ is also protected by an amino protecting group, and where required removing the protecting group(s), and recovering a compound of formula I thus obtained in free form or in salt form.

Suitable amino protecting groups are e.g. as described, for example, in "Protective Groups in Organic Synthesis", T. W. Greene et al., John Wiley & Sons Inc., Second Edition 1991. Examples of such amino protecting groups are e.g. acetyl or amino groups as used in peptide synthesis, e.g. tert.-butoxycarbonyl, carbobenzoxy, fluorenylmethoxycarbonyl, alloxycarbonyl, 1-(4,4-dimethyl-2,6-dioxocyclohexylidene)ethyl, 1-(4,4-dimethyl-2,6-dioxocyclohexylidene)-3-methylbutyl, 4-methyltrityl. (W. C. Chan and P. D. White, Fmoc solid Phase Peptide Synthesis, Oxford University Press, 2000).

Cyclisation may conveniently be performed in the presence of an aminium- or phosphonium-based derivative for in situ carboxy activation e.g. O-(benzotriazol-1-yl)N,N,N',N'-tetramethyluronium-hexafluorophosphate, benzotriazol-1-yloxytris(pyrrolidino)phosphonium hexafluorophosphate, N-[(1H-benzotriazol-1-yl)(dimethylamino)methylene]-N-methyl methanaminium tetrafluoroborate N-oxide, N-[(dimethylamino)-1H-1,2,3-triazolo[4,5-b]pyridine-1-ylmethylene]-N-methylmethanaminium, 7-azabenzotriazol-1-yloxytris(pyrrolidino)-phosphonium hexafluorophosphate. Preferably the reaction may be carried out in the presence of a base, e.g. an organic amine, e.g. N-ethyl diisopropyl amine, N-methylmorpholine, triethylamine, or tribenzyl amine, and in the presence of an auxiliary nucleophile, e.g. 1-hydroxybenzotriazole, N-hydroxysuccinimide, 3-hydroxy-3,4-dihydro-1,2,3-benzotriazine-4-one or 1-hydroxy-7-azabenzotriazole.

The cyclisation of a compound of formula II, III or IV leads to a compound of formula I in protected form, i.e. a compound of formula I wherein one or more or all amino groups present in the molecule are protected by an amino protecting group. Examples of such compounds are e.g. cyclo[(2S,4R)-4-(Boc-NH—$CH_2$—$CH_2$—NH—CO—O)-Pro-Phg-D-Trp(Boc)-Lys(Boc)-Tyr(Bzl)-Phe-], cyclo[(2S,4R)-4-(Boc-NH—$CH_2$—$CH_2$—NH—CO—O)-Pro-Phg-D-Trp-Lys(Boc)-Tyr(Bzl)-Phe-] and cyclo[(2S,4R)-4-(Boc-NH—$CH_2$—$CH_2$—NH—CO—O)-Pro-DPhg-D-Trp-Lys(Boc)-Tyr(Bzl)-Phe-].

The amino protecting groups may be removed according to methods known in the art, e.g. by cleavage, e.g. with trifluoroacetic acid; 3M HCl, EtOAc; $Me_3CCl$, phenol, $CH_2Cl_2$; 10% $H_2SO_4$, dioxane; bromocatecholborane.

Compounds of formulae II, III and IV or salts thereof are novel and form part of the invention. These compounds may be prepared by linking together by an amide bond two peptide units, each of them containing at least one amino acid in protected or unprotected form, wherein the amide bond is in such a way that the desired amino acid sequence as defined in formulae II, III or IV is obtained.

The synthesis may be performed in accordance to methods known in the art, e.g. in solution or by solid phase synthesis, starting with the first amino acid. In the solid phase synthesis, the first amino acid is attached to a resin, e.g. a commercially available polystyrene-based resin, optionally through a suitable linker, e.g. a linker which is cleavable under mild conditions to keep the side chain protection intact, e.g. an optionally substituted trityl based linker, for example 4-(hydroxyl-diphenyl-methyl)-benzoic acid wherein one of the phenyl groups may optionally be substituted, e.g. by Cl. The build-ing-up of the desired peptide chain, whether in solution or by solid phase synthesis, may be effected in conventional manner, e.g. using amino acids wherein the terminal amino groups are Fmoc-protected, the side chain amino groups where present being protected with a different amino protecting group, e.g. Boc or CBO.

When the synthesis is effected by solid phase synthesis, the built-up peptide is then removed from the resin in accordance with methods known in the art, e.g. with acetic acid; trifluoracetic acid; acetic acid-trifluoroethanol-dichloromethane; hexafluoroisopropanol in dichloromethane. A preferred process for removing the built-up peptide from the solid phase, e.g. when using a non-chlorinated trityl based linker, is e.g. the treatment with methanol/dichloromethane, preferably at room temperature, or a treatment with a ketone, e.g. ethyl methyl ketone, preferably at a temperature of about 50° C.

Examples of compounds of formulae II, III and IV are e.g.

H-Lys(Boc)-D-Tyr(Bzl)-Phe-(2S,4R)-4-(Boc-NH—$CH_2$—$CH_2$—NH—CO—O)-Pro-Phg-D-Trp(Boc)-OH

H-Lys(Boc)-D-Tyr(Bzl)-Phe-(2S,4R)-4-(Boc-NH—$CH_2$—$CH_2$—NH—CO—O)-Pro-Phg-D-Trp-OH

H-(2S,4R)-4-(Boc-NH—$CH_2$—$CH_2$—NH—CO—O)-Pro-Phg-D-Trp(Boc)-Lys(Boc)-Tyr(Bzl)-Phe-OH

H-Tyr(Bzl)-Phe-(2S,4R)-4-(Boc-NH—$CH_2$—$CH_2$—NH—CO—O)-Pro-DPhg-DTrp(Boc)-Lys(Boc)-OH

H-Tyr(Bzl)-Phe-(2S,4R)-4-(Boc-NH—$CH_2$—$CH_2$—NH—CO—O)-Pro-Phg-DTrp-Lys(Boc)-OH

H-Tyr(Bzl)-Phe-(2S,4R)-4-(Boc-NH—$CH_2$—$CH_2$—NH—CO—O)-Pro-Phg-D-Trp(Boc)Lys(Boc)-OH.

Compounds of formula II, III or IV may exist in a salt form as disclosed above for the compounds of formula I.

The compounds of formula I are valuable somatostatin agonists, and have interesting pharmacological properties as disclosed e.g. in WO 97/01579 or WO 02/10192, the contents thereof disclosing the pharmacological properties being incorporated herein by reference. A preferred compound is cyclo [{(4-$NH_2$—$C_2H_4$—NH—CO—O)-Pro}-Phg-DTrp-Lys-Tyr(4-Benzyl)-Phe], or a salt thereof. Preferred salts are the aspartate (mono- or di-aspartate) or pamoate.

When using the process of the invention, a cyclisation yield of the corresponding linear peptide of formula II, III or IV higher than 70% may be obtained.

The following examples are illustrative of the invention. All temperatures are in ° C.

The following abbreviations are used:

Bzl=benzyl

DAEM=diethylamine

DICI=diisopropyl carbodiimide

DMF=N,N-dimethylformamide

DPPA=diphenylphosphoryl azide

EDIPA=N-ethyl diisopropyl amine

HBTU=O-(benzotriazol-1-yl)-N,N,N',N'-tetramethyluronium-hexafluorophosphate

HOBT=1-hydroxy-benzotriazole

IPA=isopropyl alcohol

Phg=phenylglycine

RT=room temperature

TBME=tert-butylmethyl ether

EXAMPLE 1

[H-Tyr(Bzl)-Phe-(2S,4R)-4-(Boc-NH—CH$_2$—CH$_2$—NH—CO—O)-Pro-Phg-D-Trp-Lys(Boc)-OH]

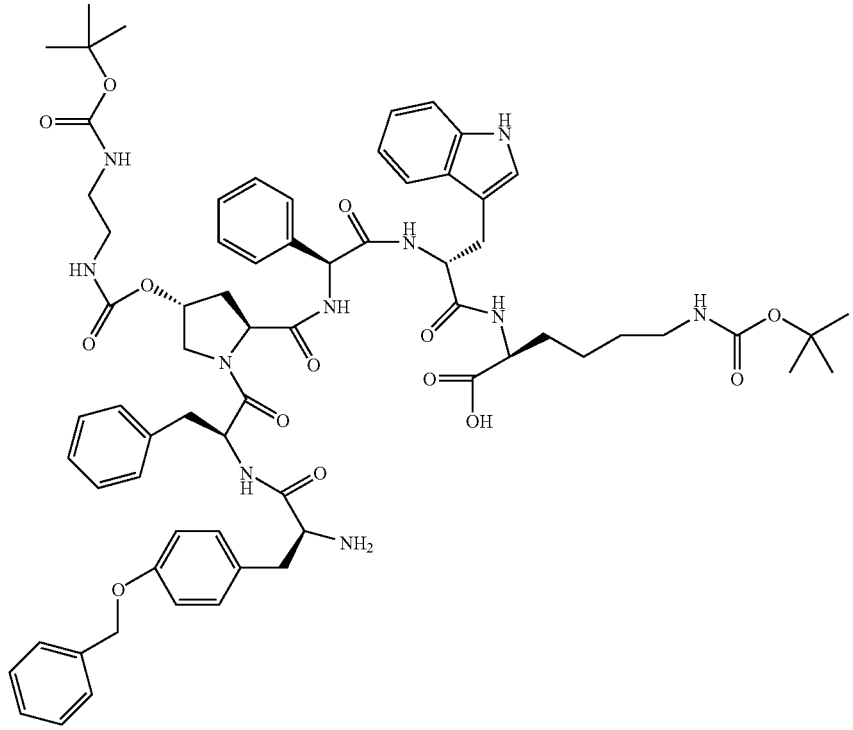

10.4 g (FMOC-Tyr(Bzl)-Phe-[(2S,4R)-4-(Boc-NH—CH$_2$—CH$_2$—NH—CO—O)]-Pro-Phg-D-Trp-Lys(BOC)-OH) are dissolved in 100 ml DMF. At RT 2.0 ml diethylamine are added and stirring continued for 4 hours at RT. The clear yellow solution is evaporated at 40°. To the residue are added 150 ml isopropyl acetate. Seeding and stirring for 18 hours at RT, filtration and washing with 20 ml isopropyl acetate. Drying at 40°. HPLC 87.5% b.a. (17.6 min). ESI-MS: 1287.5(M+Na)$^+$; $^1$H-NMR(DMSO) (∂, DMSO): 1.14(2H, m), 1.33 (2H, m), 1.37(18H, m), 1.53(1H, m), 1.64(1H, m), 2.06(1H, m), 2.22(1H, m), 2.78-3.15(12H, m), 3.38(1H, m), 3.79(2H, br), 4.12(1H, m), 4.55-4.75(3H, m), 5.06(2H, s), 5.15(1H, d), 5.54(1H, d), 6.75(1H, br), 6.83(1H, br), 6.89(2H, d), 6.94(1H, t), 6.99(1H, s), 7.43(2H, d), 7.10-7.50(arom.H), 7.59(1H, d), 8.14(1H, d), 8.45-8.55(2H, m), 8.60(1H, d), 10.71(1H, br).

The compound used as starting material is prepared as follows:

a) Z-D-Trp-Lys(BOC)-OMe

To a solution of 23.7 g Z-D-Trp-OH in 230 ml THF are added 9.5 g HOBt at RT. A clear colorless solution is formed. Then 20.8 g H-Lys(BOC)-OMe.HCl are added at RT, followed by 7.7 ml N-methylmorpholine. The fine suspension is cooled down to 0° and 11.4 ml diisopropylcarbodiimide added. Stirring 1 hour at 0°, then 3 hours at RT. A solution of 7.0 g sulfuric acid conc. in 120 ml water is added to the suspension. Extraction with 150 ml ethyl acetate, separation of the phases and washing of the organic phase consecutively with 100 ml brine saturated, 100 ml brine 25%, 5% sodium hydrogencarbonate solution. Then the organic phase is dried over MgSO4 and evaporated. The residue is taken up in 250 ml isopropyl acetate and stirred 2 hours at RT. Filtration and drying at 40° gives 40.9 g Z-D-Trp-Lys(BOC)-OMe, white substance. HPLC-conditions: MN Nucleosil 100 A/C 18; 5 micron; 250×4 mm; phase A: 0.24% phosphoric acid, phase B acetonitrile; gradient: from 20 to 80% B in 30 minutes; wavelength 220 nm; flow rate 1.3 ml/min; Temperature 35°: purity 97.8% b.a. (24.2 min).

b) H-D-Trp-Lys(BOC)-OMe

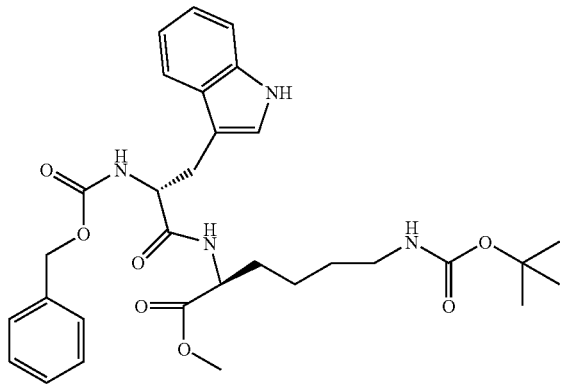

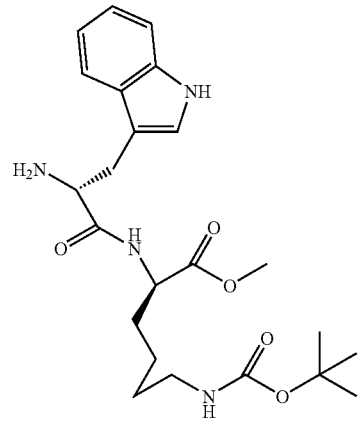

19.8 (34.1 mmol) g Z-D-Trp-Lys(BOC)-OMe are dissolved in 220 ml methanol, 2.2 g catalyst PdC 10% added and hydrogenated at RT. The hydrogenation is finished after 1 hour at RT, the catalyst filtered off and the filtrate evaporated at 30°: white solid. HPLC: 98.1% b.a. (16.2 min).

c) Z-Phg-D-Trp-Lys(BOC)-OMe

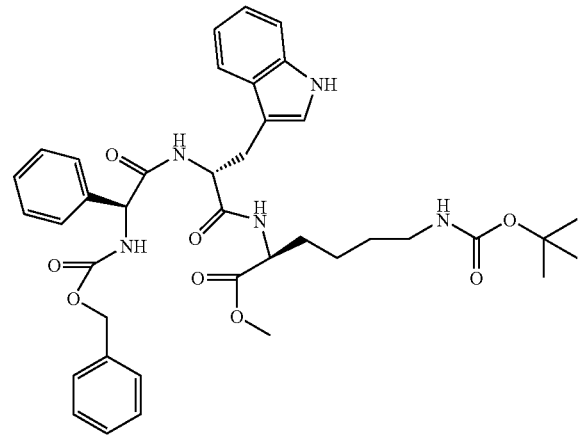

17.0 g H-D-Trp-Lys(BOC)-OMe are mixed with 80 ml THF. 9.2 g Z-Phg-OH are added to the grey suspension at RT. Addition of 4.4 g HOBt, rinsing with 20 ml THF. The turbid yellow solution is cooled down to 0° and a solution of 5.3 ml d) H-Phg-D-Trp-Lys(BOC)-OMe

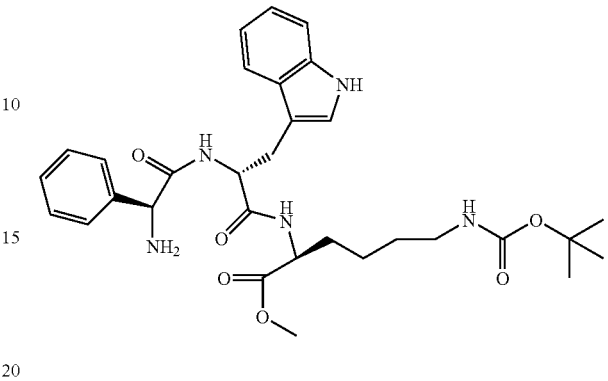

23.4 g (23.8 mmol) (Z-Phg-D-Trp-Lys(BOC)-OMe) are dissolved in 260 ml methanol, 2.6 g Pd/C 10% added and hydrogenated at RT and normal pressure. After 3 hours the catalyst is filtered off and the filtrate evaporated at 30°: white solid. HPLC 95.9% b.a. (17.6 min).

e) Z-[(2S,4R)-4-(Boc-NH—CH$_2$—CH$_2$—NH—CO—O)]-Pro-Phg-D-Trp-Lys(BOC)-OMe

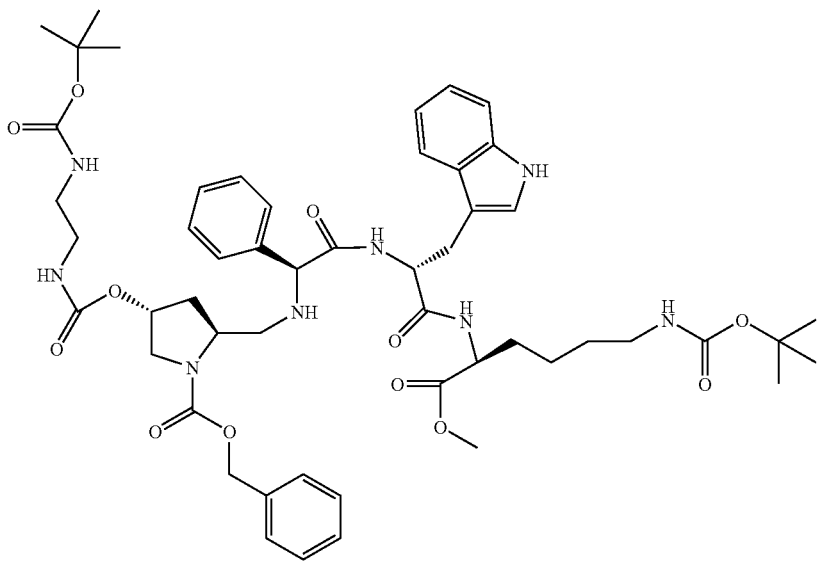

DICI in 15 ml THF added within 10 minutes. Stirring 2 hours at 0°, then 2 hours at RT. Then addition of a solution of 3.6 sulfuric acid in 57 ml water, extraction with 70 ml ethyl acetate, washing with water, saturated brine, 5% sodium hydrogencarbonate, 25% brine, drying over MgSO4 and evaporation. The white residue is stirred in 125 ml isopropyl acetate 2 hours at 40° and the suspension filtered. Drying of the residue at 40°: slightly yellow substance. HPLC: 96.3% b.a. (25.3 min).

11.1 g (2S,4R)-4-(2-tert-Butoxycarbonylaminoethylcarbamoyloxy)-pyrrolidine-1-carboxylic acid benzyl ester-2-carboxylic acid and 19.0 g H-Phg-D-Trp-Lys(BOC)-OMe are dissolved in 290 ml THF at RT. 3.32 g HOBt are added and the turbid solution cooled to 0°. A solution of 4.56 ml DICI in 90 ml THF is added. Stirring 24 hours at 0°. Then a solution of 2.2 g sulfuric acid in 22 ml water is added at RT, the slightly opal solution stirred for 15 minutes and then dropped to 500 ml water. The white suspension is evaporated at 50° until no more THF distilled. Filtration of the suspension and washing of the residue 4 times with 80 ml water each, then with 250 ml methanol and then twice with totally 80 ml methanol. Drying over night at 50°. HPLC 91.0% b.a. (19.5 min).

f) H-[(2S,4R)-4-(Boc-NH—CH$_2$—CH$_2$—NH—CO—O)]-Pro-Phg-D-Trp-Lys(BOC)-OMe 5.1 g Z-Phe-OH and 16.5 g H-[(2S,4R)-4-(Boc-NH—CH$_2$—CH$_2$—NH—CO—O)]-Pro-Phg-D-Trp-Lys(BOC)-OMe are dissolved in 250 ml THF, 2.29 g HOBT added and the dark solution cooled to 0°. 3.1 ml DICI are dissolved in 80 ml THF and added to the reaction mixture at 0°. Stirring 24 hours at 0°. The reaction mixture is added to 200 ml sulfuric

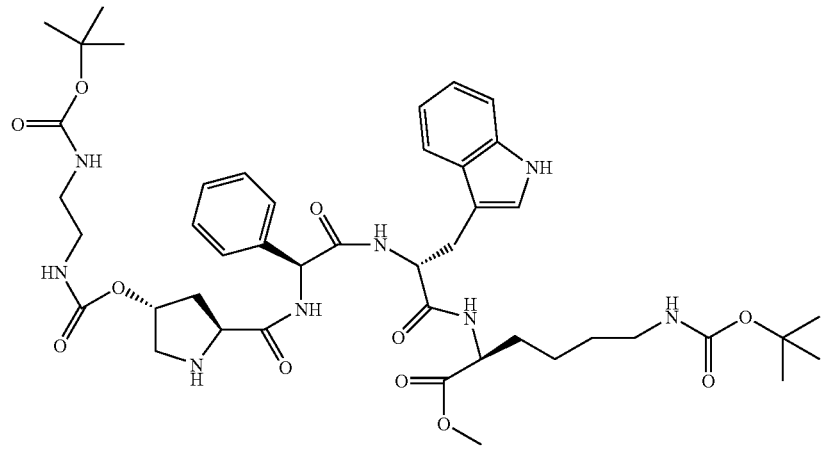

22.0 g (12.7 mmol) Z-[(2S,4R)-4-(Boc-NH—CH$_2$—CH$_2$—NH—CO—O)]-Pro-Phg-D-Trp-Lys(BOC)-OMe are dissolved in 220 ml DMF and 4.4 g Pd/C 10% added. Hydrogenation 4 h at RT. Then the catalyst is filtered off and the filtrate added to a mixture of 600 g ice and 400 ml water. The precipitated product is filtered off and washed with water. Drying at 30° gives a grey solid. HPLC: 97.0% b.a. (12.3 min).

acid 10%, the precipitated solids filtered off and ished with water. After filtration the residue is mixed with 200 ml methanol and the suspension filtered off. Drying at 40° HPLC: 97.2% b.a. (21.1 min).

g) Z-Phe-[(2S,4R)-4-(Boc-N H—CH$_2$—CH$_2$—NH—CO—O)]-Pro-Phg-D-Trp-Lys(BOC)-OMe

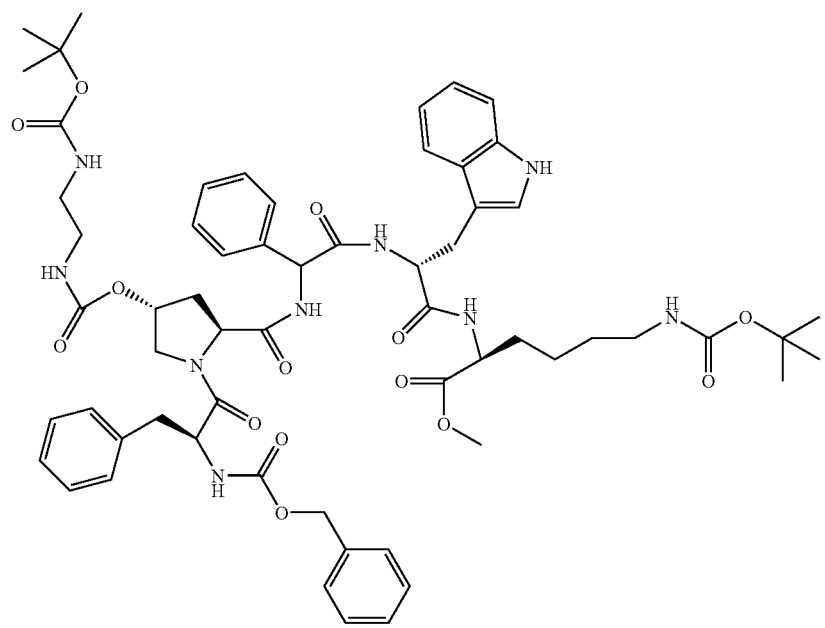

h) (H-Phe-[(2S,4R)-4-(Boc-NH—CH$_2$—CH$_2$—NH—CO—O)]-Pro-Phg-D-Trp-Lys(BOC)-OMe)

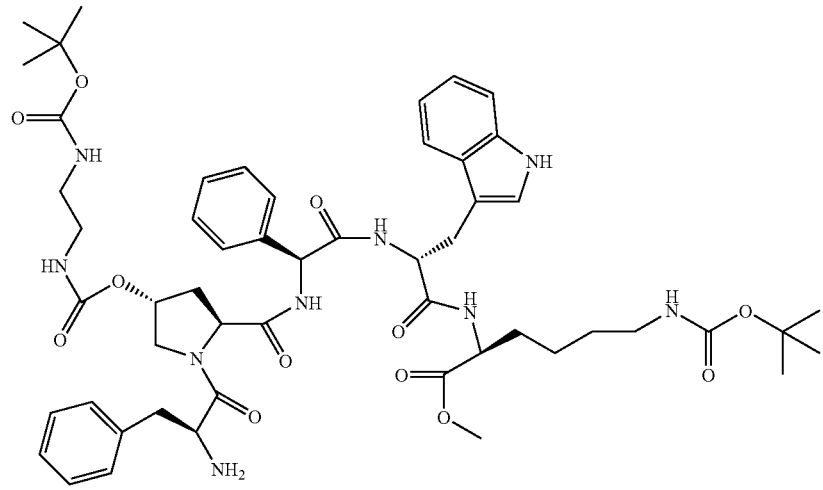

8.5 g Z-Phe-[(2S,4R)-(Boc-NH—CH$_2$—CH$_2$—NH—CO—O)]-Pro-Phg-D-Trp-Lys(BOC)-OMe are dissolved in 180 ml DMF, 4.25 g Pd/C 10% added and the mixture hydrogenated at RT for 6 hours. Then the catalyst is filtered off and the filtrate evaporated at 40°. To the residue (30 g) 600 ml t-butyl methyl ether are dropped at RT, the suspension filtered and the residue washed with 300 ml TBME. Drying at 40° HPLC 93.1% b.a. (16.6 min).

i) FMOC-Tyr(Bzl)-Phe-[(2S,4R)-4-(BOC-NH—CH$_2$—CH$_2$—NH—CO—O)]-Pro-Phg-D-Trp-Lys(BOC)-OMe

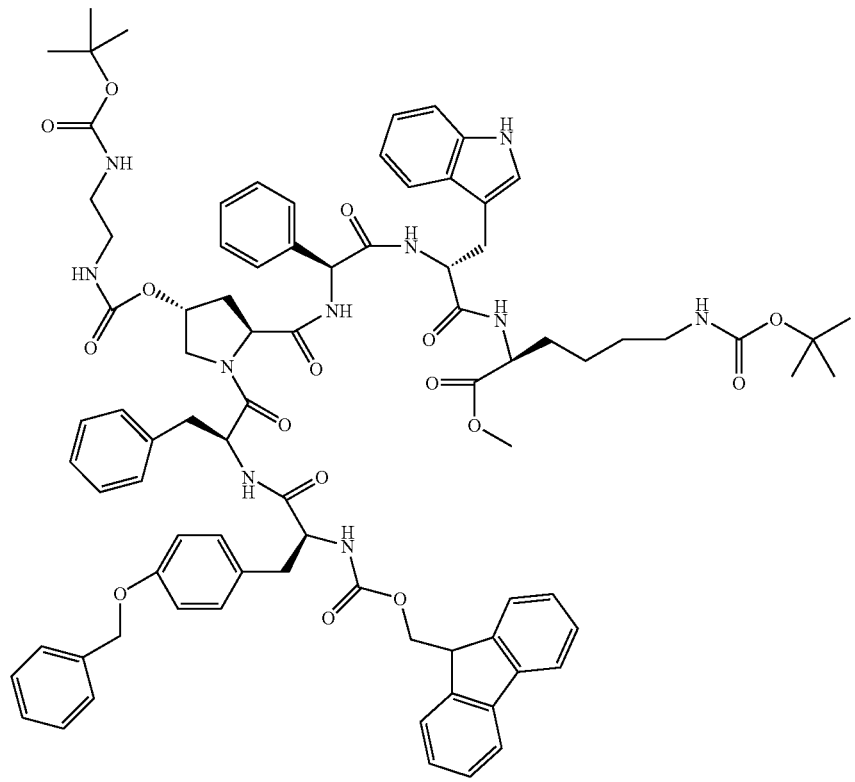

6.5 g H-Phe-[(2S,4R)-4-(Boc-NH—CH$_2$—CH$_2$—NH—CO—O)]-Pro-Phg-D-Trp-Lys(BOC)-OMe and 3.1 g FMOC-Tyr(Bzl)-OH and 0.86 g HOBT are suspended in 180 ml THF and cooled down to 0°. 5.5 g LiBr are added and then 20 ml THF. Then 1.18 ml DICI dissolved in 50 ml THF are added and the dark suspension stirred at 0° for 2 hours. The cooling bath is removed and stirring continued for 24 hours. Then a solution of 0.65 g sulfuric acid and 6.5 ml water are added, then 160 ml water. Evaporation at 40°, filtration of the residue, washing with water until the last ish-water had a pH of 4.0. The filter cake is stirred in 30 ml methanol, the suspension filtered and the residue washed with 10 ml methanol. Drying at 35° gives a grey substance. HPLC 95.4% b.a. (26.0 min).

10) FMOC-Tyr(Bzl)-Phe-[(2S,4R)-4-(Boc-NH—CH$_2$—CH$_2$—NH—CO—)]-Pro-Phg-D-Trp-Lys(BOC)-OH

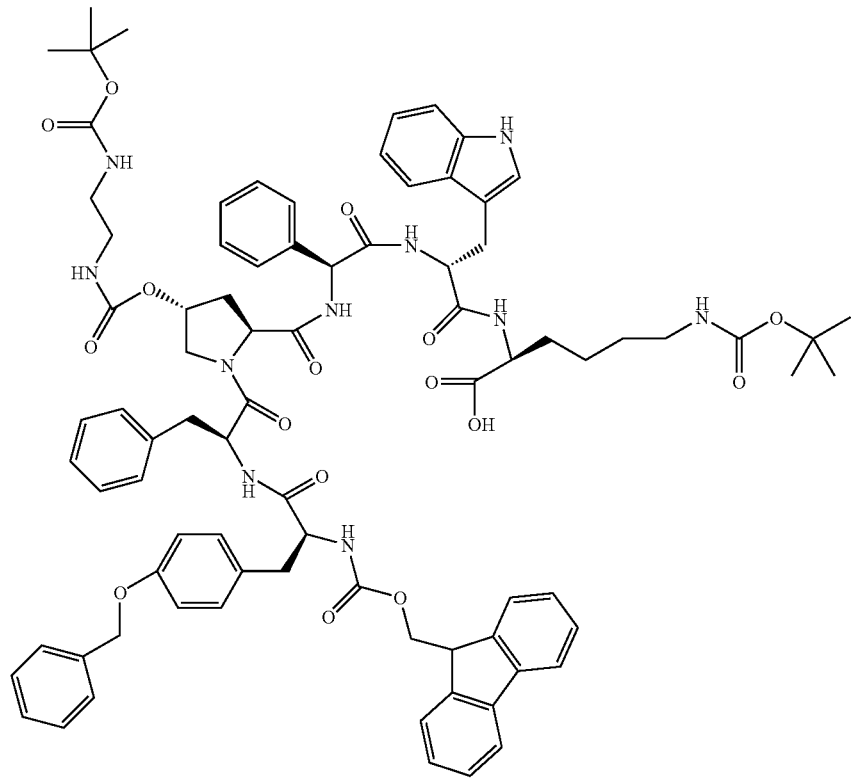

13.0 g FMOC-Tyr(Bzl)-Phe-[(2S,4R)-4-(Boc-NH—CH$_2$—CH$_2$—NH—CO—O)]-Pro-Phg-D-Trp-Lys(BOC)-OMe are suspended in 250 ml THF. 7.3 g LiBr and 75 ml THF are added. Then 8.7 ml NaOH 1 molar is slowly added at RT within 20 minutes. Stirring at RT is continued for 3 hours, then additional 5 ml NaOH 1 molar are added within the next 15 hours. The final reaction solution is added to a solution of 1.7 g sulfuric acid in 34 ml water. The resulting 2-phase-mixture is added to 50 ml ethyl acetate. After phase separation the organic phase is 3 times washed with brine and then evaporated. To the residue are added 25 ml DIF. The resulting clear DIF-solution is added to 260 ml water. The resulting suspension is filtered and the filter cake washed three times with water and dried over night at 40°. HPLC 71.9% b.a. (28.6 min).

EXAMPLE 2

Preparation of 4-(Chloro(diphenyl)methyl)benzoyl aminomethyl polystyrene resin

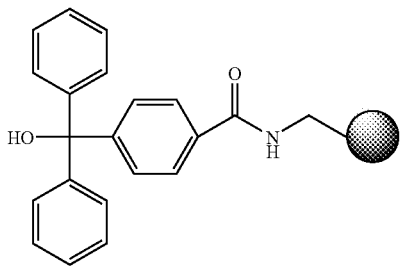

The synthesis is carried out in a manually operated 1 L stirred batch reactor equipped with sintered glass frit under nitrogen. Commercial available aminomethylpolystyrene resin (30.4 g, 41.07 mmol), pretreated with DMF, reacted at RT overnight with a solution of 4-(hydroxyl-diphenyl-methyl)benzoic acid (15.0 g, 49.28 mmol, 1.2 equiv.), hydroxybenzotriazole (HOBT) (7.54 g, 49.28 mmol, 1.2 equiv.) and DICI (12.43 g, 98.57 mmol, 2.4 equiv.) in DMF (140 ml). Solvent is removed by filtration through the frit under reduced pressure, and the resin is washed by turns five times with DMF and five times with methanol. Drying in vacuum at 40° yields 44.69 g resin. This resin is used as starting material for the following synthesis of the hexapetides.

Procedure for the Synthesis of the Protected Linear Peptide

The resin-linked linear hexapeptides are assembled manually in the C- to N direction by iterative coupling reactions in a stirred batch reactor equipped with sintered glass frit under nitrogen. 4-(Chloro(diphenyl)methyl)benzoyl aminomethyl polystyrene resin is used as starting material and carried through a standard protocol consisting of repetitive cycles of Nα-deprotection (20% v/v diethylamine (DAEM) in DMF), repeated washings with DMF and IPK in turns, and couplings (DIPCI/HOBT, DIEPA und DMF) at RT. In slight modification of this coupling procedure, special care is taken to minimize racemisation of phenylglycine by carrying out coupling of this amino acid at 0°. Before cleavage of the completely assembled protected linear peptide from its resin support, Nα-Fmoc protection is removed.

Fmoc-(2S,4R)-4-(Boc-NH—CH$_2$—CH$_2$—NH—CO—O)-Pro-OH is synthesized as disclosed in WO02/101192. All other amino acids are commercial available.

Synthesis of H-Tyr(Bzl)-Phe-(2S,4R)-4-(Boc-NH—CH$_2$—CH$_2$—NH—CO—O)-Pro-Phg-D-Trp(Boc) Lys(Boc)-OH

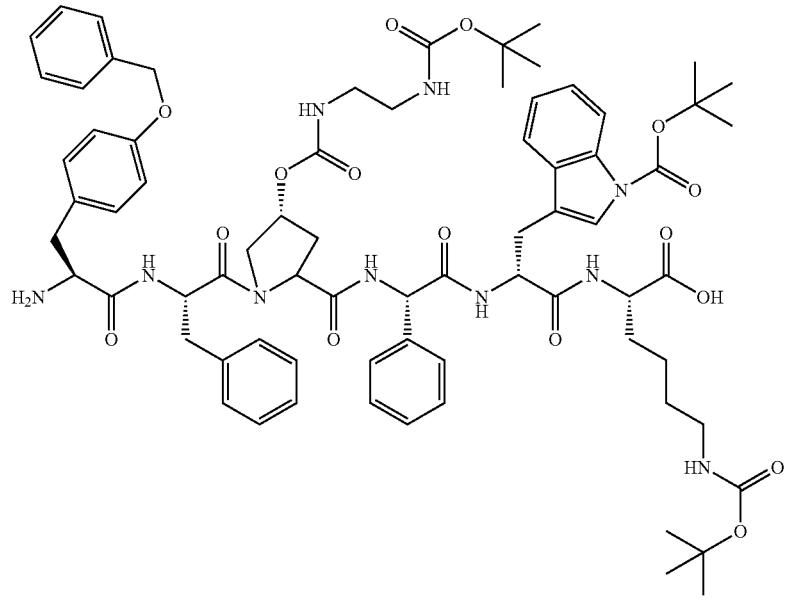

a) Synthesis of Fmoc-Lys(Boc)-O-resin 4-(Chloro(diphenyl)methyl)benzoyl aminomethyl polystyrene resin (20 g, 19.4 mmol), pretreated with toluene, is treated for 4 hours with acetyl chloride (7.6 g, 97 mmol) in toluene at RT. After filtration, the procedure is repeated overnight, thereafter, the resin is filtered and washed with toluene and dichloromethane. Coupling is carried out with a mixture of Fmoc-Lys(Boc)-OH (18.2 g, 38.8 mmol; 2 equiv.) and N-methylmorpholine (3.94 g, 38.8 mmol, 2 equiv.) for 4 hours at RT. After filtration, the resin is washed with DMF and IPA 3 times in turns and dried in vacuum to get 26.5 g of a yellowish Fmoc-Lys(Boc)-O-resin with a capacity of 0.566 mmol/g (determined with the Fmoc-method).

(Lit. Fmoc-method: Meienhofer, J.; Waki, M; Heimer, E. P.; Lambros, T. J.; Makofske, R. C.; Chang, C. D. Int. J. Pep. Prot. Res. 1979, 13, 35)

b) Resin-O-Lys(Boc)-D-Trp(Boc)-Phg-(2S,4R)-4-(Boc-NH—CH$_2$—CH$_2$—NH—CO—O)-Pro-Phe-Tyr(Bzl)-H Fmoc-Lys(Boc)-O-resin (28.0 g, 19.96 mmol) is suspended in DMF and treated with a solution of DAEM in DMF (20% v/v) for 10 minutes at RT. After being filtered, the procedure is repeated and then washed with DMF and IPA 3 times in turns, followed by 3 times washings with DMF. This procedure of Nα-Fmoc-deprotection and washings is repeated after each coupling step.

Coupling is carried out with a mixture of amino acid, HOBT and DICI which is stirred 30 minutes at RT, and then added to the resin at once. Coupling is continued until completion, i.e. until complete disappearance of residual amino groups is monitored by negative "Kaiser" Ninhydrin test. After being coupled, the resin is washed 5 times with DMF, and is then ready for Fmoc-protection.

The following amino acid-derivatives are sequentially coupled:

Fmoc-D-Trp(Boc)-OH (16.81 g, 31.92 mmol, 2 equiv.), DIF (100 ml), HOBT (4.93 g, 32.24 mmol, 2.02 equiv.), DICI (5.35 g, 42.45 mmol, 2.66 equiv.).

Fmoc-Phg-OH (11.92 g, 31.92 mmol, 2 equiv.), THF (70 ml), HOBT (4.93 g, 32.24 mmol, 2.02 equiv.), DICI (5.35 g, 42.45 mmol, 2.66 equiv.). Special care is taken to minimize racemisation of phenylglycine by carrying out coupling of this amino acid at 0° C.

Fmoc-(2S,4R)4-(Boc-NH—CH$_2$—CH$_2$—NH—CO—O)-Pro-OH (17.26 g, 31.92 mmol, 2 equiv.), DIF (100 ml), HOBT (4.93 g, 32.24 mmol, 2.02 equiv.), DICI (5.35 g, 42.45 mmol, 2.66 equiv.).

Fmoc-Phe-OH (12.36 g, 31.92 mmol, 2 equiv.), DIF (100 ml), HOBT (4.93 g, 32.24 mmol, 2.02 equiv.), DICI (5.35 g, 42.45 mmol, 2.66 equiv.).

Fmoc-Tyr(Bzl)-OH (15.75 g, 31.92 mmol, 2 equiv.), DIF (100 ml), HOBT (4.93 g, 32.24 mmol, 2.02 equiv.), DICI (5.35 g, 42.45 mmol, 2.66 equiv.).

Before cleavage of the completely assembled protected linear peptide from its resin support, Nα-Fmoc protection is removed by treating the resin with a solution of DAEM in DMF (20% v/v) for 10 minutes at RT. After being filtered, the procedure is repeated and washed with DMF and IPA 3 times in turns, followed by 3 times washings with DMF.

(Drying of the Resin in Vacuum at 40° C. Gives a Yellowish Resin).

c) Cleavage of the Linear Peptide from its Resin Support

H-Tyr(Bzl)-Phe-(2S,4R)-4-(Boc-NH—CH$_2$—CH$_2$—NH—CO—O)-Pro-Phg-D-Trp(Boc)Lys(Boc)-OH

Ca) Method with AcOH/CH$_2$Cl$_2$/H$_2$O 45/45/5 v/v/v

The completely assembled protected linear peptide resin-O-Lys(Boc)-D-Trp(Boc)-Phg-(2S,4R)-4-(Boc-NH—CH$_2$—CH$_2$—NH—CO—O)-Pro-Phe-Tyr(Bzl)-H (24.5 g) is suspended in a mixture of AcOH/CH$_2$Cl$_2$/H$_2$O 45/45/5 v/v/v (150 ml) and stirred for one hour at RT, filtered and washed with CH$_2$Cl$_2$. The filtrate is evaporated to dryness, the residue is stirred for one hour with a mixture of TBME and heptane 7/3 v/v, filtered and dried in vacuum. A yellowish solid is obtained; content: 93.5% HPLC g/g; purity 91.6% (F)-HPLC and 2.5% (F)-HPLC D-Phg-Epimer.

The resin (4-(Chloro(diphenyl)methyl)benzoyl aminomethyl polystyrene resin) is washed 3 times with methanol and dried and could be reused.

Cb) Method with CH$_2$Cl$_2$ and MeOH

The completely assembled protected linear peptide resin-O-Lys(Boc)-D-Trp(Boc)-Phg-(2S,4R)-4-(Boc-NH—CH$_2$—CH$_2$—NH—CO—O)-Pro-Phe-Tyr(Bzl)-H (6.2 g) is suspended in a mixture of CH$_2$Cl$_2$/MeOH 1/1 v/v (115 ml) and stirred for 3 days at RT, filtered and washed with CH$_2$Cl$_2$. The filtrate is evaporated to dryness, the residue is stirred for one hour with a mixture of TBME and heptane 7/3 v/v (60 ml), filtered and dried in vacuum. Content: 93.5% HPLC g/g; purity 92.6% (F)-HPLC and 1.1% (F)-HPLC D-Phg-Epimer.

The resin (4-(Chloro(diphenyl)methyl)benzoyl aminomethyl polystyrene resin) is washed 3 times with methanol and dried and could be reused.

Cc) Method with Ethyl Methyl Ketone/MeOH

The completely assembled protected linear peptide resin-O-Lys(Boc)-D-Trp(Boc)-Phg-(2S,4R)-4-(Boc-NH—CH$_2$—CH$_2$—NH—CO—O)-Pro-Phe-Tyr(Bzl)-H (4.0 g) is suspended in a mixture of diethyl methyl ketone 1/1 v/v (24 ml) and stirred for 15 hours at 50° C., filtered and washed with MeOH. The filtrate is evaporated to dryness, the residue is stirred for one hour with a mixture of TBME and heptane 7/3 v/v (60 ml), filtered and dried in vacuum. Content: 88.1% HPLC g/g; purity 95.2% (F)-HPLC and 1.8% (F)-HPLC D-Phg-epimer.

The resin (4-(Chloro(diphenyl)methyl)benzoyl aminomethyl polystyrene resin) is washed 3 times with methanol and dried and could be reused.

Purification

For analytical purposes the linear peptides were purified by RP chromatography.

Characterization

The structure of a analytical sample purified by RP-chromatography is confirmed by FAB-MS, LC-MS and NMR-data (DMSO in ppm, 1.16, 1.34, 1.55, 1.61 (3H), 1.66, 2.05, 2.20, 2.51, 2.83 (2H), 2.91, 2.96, 2.98, 3.02, 3.41, 3.78, 4.13, 4.61, 5.13, 5.51, 6.74, 6.83, 6.88 (2H), 7.01 (2H), 7.11 (2H), 7.38, 7.42 (2H), 7.49, 7.72, 8.01, 8.29, 8.48, 8.62, 8.75.)

The amino acid configuration is determined by amino acid analysis: the compound is hydrolyzed under acidic conditions, converted to derivatives and the configuration of the each individual amino acid is assigned by enantioselective gas chromatography/chemical ionization mass spectrometry.

Additional proof of structure is the conversion of the different linear peptides to well characterized cyclic peptide.

The following compounds were synthesized according to the described procedure.

H-Lys(Boc)-Tyr(Bzl)-Phe-(2S,4R)-4-(Boc-NH—CH$_2$—CH$_2$—NH—CO—O)-Pro-Phg-D-Trp(Boc)-OH;

H-Lys(Boc)-Tyr(Bzl)-Phe-(2S,4R)-4-(Boc-NH—CH$_2$—CH$_2$—NH—CO—O)-Pro-Phg-D-Trp-OH;

H-(2S,4R)-4-(Boc-NH—CH$_2$—CH$_2$—NH—CO—O)-Pro-Phg-D-Trp(Boc)-Lys(Boc)-Tyr(Bzl)-Phe-OH;

H-Phe-(2S,4R)-4-(Boc-NH—CH$_2$—CH$_2$—NH—CO—O)-Phg-D-Trp(Boc)-Lys(Boc)-Try(Bzl)-OH;

H-Tyr(Bzl)-Phe-(2S,4R)-4-(Boc-NH—CH$_2$—CH$_2$—NH—CO—O)-Pro-DPhg-DTrp(Boc)-Lys(Boc)-OH

EXAMPLE 3

Cyclisation of the Linear Protected Peptides to Synthesize

Cyclo[(2S,4R)-4-(Boc-NH—CH$_2$—CH$_2$—NH—CO—O)-Pro-Phg-D-Trp(Boc)-Lys(Boc)-Tyr(Bzl)-Phe-]

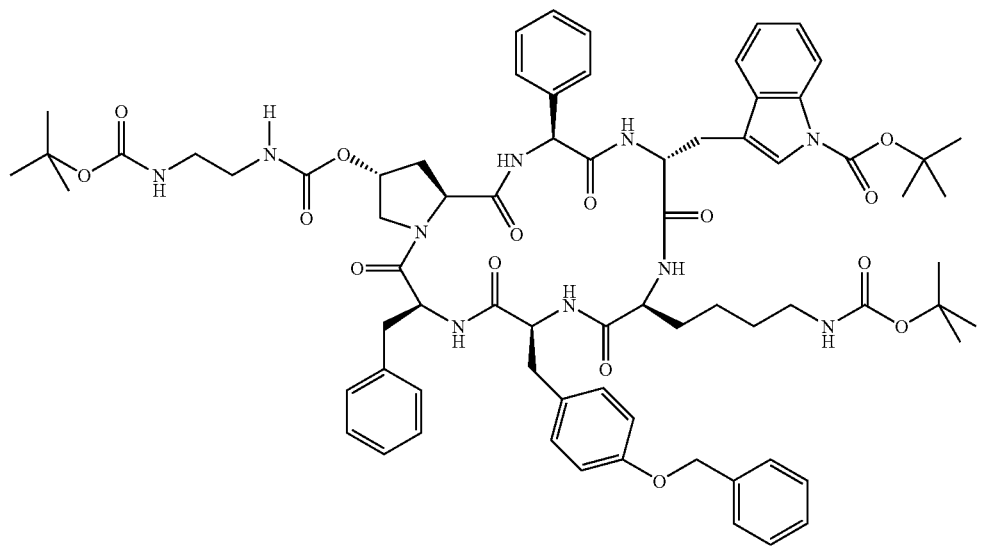

Cyclisation of H-Phe-(2S,4R)-4-(Boc-NH—CH₂—CH₂—NH—CO—O)-Pro-Phg-D-Trp(Boc)-Lys(Boc)-Tyr(Bzl)-OH Azide-Method For cyclisation, the linear fragment (2.5 g, 1.83 mmol) is dissolved in DMF (391 ml), cooled to −5°, treated with EDIPA (0.47 g, 3.66 mmol, 2 equiv.) and DPPA (0.75 g, 2.75 mmol, 1.5 equv.), and stirred at that temperature until completion (app. 20 h). Water (391 ml) is added dropwise to the reaction mixture, the precipitation is filtered and washed with water until no azide is detectable. 4.9 g of water wet white solid (Rf of HPLC identical to reference) is obtained, which is used in the deprotection reaction without further purification. The compound is characterized by direct comparison with a reference compound by HPLC.

Cyclisation of H-Tyr(Bzl)-Phe-(2S,4R)-4-(Boc-NH—CH₂—CH₂—NH—CO—O)-Pro-Phg-D-Trp(Boc)Lys(Boc)-OH a) HBTU Method a For cyclization the linear fragment (6.0 g, 3.5 mmol) is dissolved in DMF (780 ml), cooled to −5°, treated with EDIPA (1.13 g, 8.75 mmol, 2.5 equiv.), HOBT (1.18 g, 8.75 mmol, 2.5 equiv.), HBTU (3.3 g, 8.78 mmol, 2.5 equiv.) and stirred at that temperature until completion (app. 2 h). Water (391 ml) is added drop wise to the reaction mixture at RT, the precipitation is filtered and washed with water and heptane and dried in vacuum overnight. 5.4 g white, yellow solid is obtained. The compound is characterized by direct comparison with a reference compound by HPLC. Content 55% w/w HPLC, purity 78 (A %)-HPLC.

b) HBTU Method b

For cyclisation, the linear fragment (6.0 g, 4.16 mmol) is dissolved in DMF (60 ml) and is dropped into a mixture of HOBT (4.15 g, 10.4 mmol, 2.5 equiv.), HBTU (4.15 g, 10.4 mmol, 2.5 equiv.) and EDIPA (1.41 g, 10.4 mmol, 2.5 equiv.) in DMF (135 ml) at −5° and stirred at that temperature until completion (app. 2 h). Water (559 ml) is added dropwise to the reaction mixture at RT, the precipitation is filtered and washed with water and heptane and dried in vacuum overnight. A white, yellow solid is obtained. The compound is characterized by direct comparison with a reference compound by HPLC. Content 77% w/w HPLC, purity 84 (A %)-HPLC.

The following linear peptides are cyclized in accordance with above procedure:

H-Lys(Boc)-Tyr(Bzl)-Phe-(2S,4R)-4-(Boc-NH—CH₂—CH₂—NH—CO—O)-Pro-Phg-D-Trp(Boc)-OH

H-Lys(Boc)-Tyr(Bzl)-Phe-(2S,4R)-4-(Boc-NH—CH₂—CH₂—NH—CO—O)-Pro-Phg-D-Trp-OH

H-(2S,4R)-4-(Boc-NH—CH₂—CH₂—NH—CO—O)-Pro-Phg-D-Trp(Boc)-Lys(Boc)-Tyr(Bzl)-Phe-OH

H-Phe-(2S,4R)-4-(Boc-NH—CH₂—CH₂—NH—CO—O)-Phg-D-Trp(Boc)-Lys(Boc)-Try(Bzl)-OH

H-Tyr(Bzl)-Phe-(2S,4R)-4-(Boc-NH—CH₂—CH₂—NH—CO—O)-Pro-DPhg-DTrp(Boc)-Lys(Boc)-OH

EXAMPLE 4

Synthesis of Cyclo[(2S,4R)-4-(Boc-NH—CH₂—CH₂—NH—CO—O)-Pro-Phg-D-Trp-Lys-Tyr(Bzl)-Phe-]trifluoroacetic acid salt

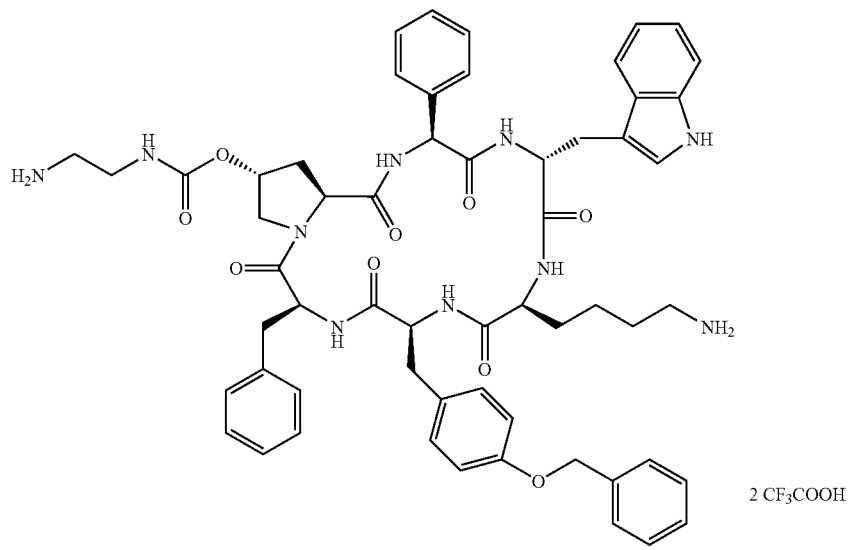

2 CF₃COOH

For complete deprotection, the residue (1.5 g, 0.79 mmo) is dissolved at 0° in TFA/H$_2$O 95:5 (8.3 ml), and the mixture is stirred in the cold for 30 minutes. The cold reaction mixture is dropped into a mixture of TBME (29 ml) and heptane (13 ml) at RT, and stirred for 2 hours. The precipitation is filtered, washed with TBME/heptane 1:1 (v/v) and dried in vacuum. A beige solid is obtained, content 53% w/w HPLC, purity: 79 (A %)-HPLC.

The invention claimed is:

1. A process for producing a compound of formula I wherein
  R$_1$ is —C$_{2-6}$alkylene-NR$_3$R$_4$, —C$_{2-6}$alkylene-guanidine or —C$_{2-6}$alkylene-COOH wherein each of R$_3$ and R$_4$ independently is H, C$_{1-4}$alkyl, ω-hydroxy-C$_{2-4}$alkylene oracyl or R$_3$ and R$_4$ form together with the nitrogen atom to which they are attached a heterocyclic group which may comprise a further heteroatom, and
  R$_2$ is Z$_1$-CH$_2$—R$_5$, —CH$_2$—CO—O—CH$_2$—R$_5$, wherein Z$_1$ is O or S and R$_5$ is optionally substituted phenyl, or a salt thereof, comprising cyclizing a linear somatostatin analogue of formula II $$\text{H}_2\text{N}-\text{CH}-\text{CO}-\text{Phe}-\{4\text{-}(R_1-\text{NHCO}-\text{O})\text{-Pro}\}\text{-(D or L)Phg-DTrp}(R_{11})-\text{Lys}(4\text{-NHR}_{12})-\text{OH} \quad \text{II}$$
$$|$$
$$\text{CH}_2-R_2$$

with a cyclizing agent selected from O-(benzotriazol-1-yl)-N,N,N',N'-tetramethyluronium-hexaflurophosphate and 1-hydroxybenzotriazole, wherein R$_1$ and R$_2$ are as defined above, each of R$_{11}$ and R$_{12}$, independently, is an amino protecting group whereby when R$_1$ comprises a terminal NH$_2$, this terminal NH$_2$ is also protected by an amino protecting group, and where required removing the protecting group(s), and recovering a compound of formula I thus obtained in free form or in salt form.

2. A process according to claim 1 comprising cyclizing a linear somatostatin analogue of formula II $$\text{H}_2\text{N}-\text{CH}-\text{CO-Phe-}\{4\text{-}(R_1-\text{NHCO}-\text{O})\text{-Pro}\}\text{-(D or L)Phg-DTrp}(R_{11})\text{-Lys}(4\text{-NHR}_{12})-\text{OH} \quad \text{II}$$
$$|$$
$$\text{CH}_2-R_2$$

wherein R$_1$ is —CH$_2$—CH$_2$—NR$_3$R$_4$, R$_2$ is 4-benzyloxy-phenyl, and R$_3$, R$_4$, R$_{11}$ and R$_{12}$ are as defined in claim 1, whereby when R$_1$ comprises a terminal NH$_2$, this terminal NH$_2$ is also protected by an amino protecting group, and where required removing the protecting group(s), and recovering a compound of formula I thus obtained in free form or in salt form wherein R$_1$ is —CH$_2$—CH$_2$—NR$_3$R$_4$ and R$_2$ is 4-benzyloxy-phenyl.

3. A compound of formula II according to claim 2 which is selected from
  H-Tyr(Bzl)-Phe-(2S,4R)-4-(Boc-NH—CH$_2$—CH$_2$—NH—CO—O)-Pro-DPhg-DTrp(Boc)-Lys(Boc)-OH,
  H-Tyr(Bzl)-Phe-(2S,4R)-4-(Boc-NH—CH$_2$—CH$_2$—NH—CO—O)-Pro-Phg-DTrp-Lys(Boc)-OH and
  H-Tyr(Bzl)-Phe-(2S,4R)-4-(Boc-NH—CH$_2$—CH$_2$—NH—CO—O)-Pro-Phg-D-Trp(Boc)Lys(Boc)-OH or a salt thereof.

* * * * *

UNITED STATES PATENT AND TRADEMARK OFFICE
CERTIFICATE OF CORRECTION

| | | |
|---|---|---|
| PATENT NO. | : 7,615,609 B2 | Page 1 of 1 |
| APPLICATION NO. | : 10/567299 | |
| DATED | : November 10, 2009 | |
| INVENTOR(S) | : Heribert Hellstern et al. | |

It is certified that error appears in the above-identified patent and that said Letters Patent is hereby corrected as shown below:

On the Title page,

Item [*] Notice: Subject to any disclaimer, the term of this patent is extended or adjusted under 35 U.S.C. 154(b) by 136 days.

Delete the phrase "by 136 days" and insert -- by 195 days --

Signed and Sealed this

Thirty-first Day of August, 2010

David J. Kappos
*Director of the United States Patent and Trademark Office*